US009243990B2

(12) United States Patent
Durant et al.

(10) Patent No.: US 9,243,990 B2
(45) Date of Patent: Jan. 26, 2016

(54) PRESSURE REGULATORS WITH FILTER CONDITION DETECTORS

(71) Applicant: Emerson Process Management Regulator Technologies, Inc., McKinney, TX (US)

(72) Inventors: Tony Alan Durant, McKinney, TX (US); James Curtis Bagby, McKinney, TX (US); Samuel Harold Larsen, Murphy, TX (US); Anthony Francis Hartman, McKinney, TX (US)

(73) Assignee: Emerson Process Management Regulator Technologies, Inc., McKinney, TX (US)

( * ) Notice: Subject to any disclaimer, the term of this patent is extended or adjusted under 35 U.S.C. 154(b) by 173 days.

(21) Appl. No.: 13/888,039

(22) Filed: May 6, 2013

(65) Prior Publication Data

US 2014/0261795 A1 Sep. 18, 2014

Related U.S. Application Data

(60) Provisional application No. 61/791,183, filed on Mar. 15, 2013.

(51) Int. Cl.
| | |
|---|---|
| *F16K 31/12* | (2006.01) |
| *G01N 15/08* | (2006.01) |
| *F16K 37/00* | (2006.01) |
| *G05D 16/06* | (2006.01) |
| *B01D 46/00* | (2006.01) |

(52) U.S. Cl.
CPC ............ *G01N 15/08* (2013.01); *F16K 37/0091* (2013.01); *G05D 16/06* (2013.01); *B01D 46/0086* (2013.01); *Y10T 137/8158* (2015.04); *Y10T 137/8326* (2015.04)

(58) Field of Classification Search
CPC .... F16K 37/0091; G01N 15/08; G05D 16/06; Y10T 137/8158; Y10T 137/8326; B01D 46/0086
USPC .................................. 137/551, 557, 505, 544
See application file for complete search history.

(56) References Cited

U.S. PATENT DOCUMENTS

| | | | | |
|---|---|---|---|---|
| 3,828,812 | A * | 8/1974 | Read ............................. | 137/557 |
| 3,992,296 | A * | 11/1976 | Nobuta ......................... | 210/90 |
| 4,026,153 | A * | 5/1977 | Silverwater ................... | 116/204 |
| 5,817,231 | A * | 10/1998 | Souza .......................... | 210/96.2 |
| 8,097,128 | B1 * | 1/2012 | Sherry ........................... | 203/11 |
| 2003/0033106 | A1 * | 2/2003 | Von Der Hardt et al. ..... | 702/114 |
| 2003/0034305 | A1 * | 2/2003 | Luehmann et al. ........... | 210/646 |
| 2009/0050218 | A1 * | 2/2009 | Burgess et al. ............... | 137/557 |
| 2009/0182263 | A1 * | 7/2009 | Burbank et al. ............... | 604/28 |
| 2010/0017148 | A1 * | 1/2010 | Bos et al. ....................... | 702/24 |

FOREIGN PATENT DOCUMENTS

CN 2683966 Y * 3/2005

OTHER PUBLICATIONS

English Language Abstract for CN 2683966Y (from Espacenet website retrieved Jun. 24, 2015).*

* cited by examiner

*Primary Examiner* — Jessica Cahill
(74) *Attorney, Agent, or Firm* — Hanley, Flight & Zimmerman, LLC

(57) ABSTRACT

Example pressure regulators with filter condition detectors are described herein. In one example described here, a regulator includes a body having an inlet and an outlet and a flow control member interposed between the inlet and the outlet to regulate a fluid pressure at the outlet. The example regulator also includes a filter disposed between the inlet and the flow control member and a detector having a first measurement point upstream from the filter and a second measurement point downstream from the filter and upstream from the flow control member.

20 Claims, 4 Drawing Sheets

PRESSURE REGULATORS WITH FILTER CONDITION DETECTORS

CROSS-REFERENCE TO RELATED APPLICATION

This application claims the benefit under 35 U.S.C. §119(e) to U.S. Provisional Application 61/791,183 titled "PRESSURE REGULATORS WITH FILTER CONDITION DETECTORS," filed Mar. 15, 2013, which is incorporated herein by this reference in its entirety.

FIELD OF THE DISCLOSURE

The present disclosure relates generally to pressure regulators and, more specifically, to pressure regulators with filter condition detectors.

BACKGROUND

Fluid control devices, such as fluid regulators and control valves, are commonly distributed throughout process control systems to control fluid flow rates and/or pressures of various process fluids (e.g., liquids, gasses, etc.). For example, fluid regulators are typically used to regulate the pressure of a fluid to a lower and/or substantially constant value. Specifically, a fluid regulator has an inlet that typically receives a supply fluid at a relatively high pressure and provides a relatively lower and/or substantially constant pressure at an outlet. As the high pressure process fluid travels through the process control system, the regulator reduces the pressure of the process fluid at one or more points to supply a process fluid having a lower or reduced pressure to a sub-system or other custody transfer points. For example, a regulator associated with a piece of equipment (e.g., a boiler) may receive a fluid (e.g., gas) having a relatively high and somewhat variable pressure from a fluid distribution source and may regulate the fluid to have a lower, substantially constant pressure suitable for safe, efficient use by the equipment. A regulator typically reduces inlet pressure to a lower outlet pressure by restricting fluid flow through an orifice to match the fluctuating downstream demand.

Process fluids often contain unwanted particulate such as, for example, dirt, oil, and debris that cause increased wear and/or erosion on the process control system components and negatively affect operation of the entire system. Some known regulators utilize a filter disposed before the orifice to reduce particulate (e.g., dirt, oil, debris, etc.) through the regulator and, thus, to the downstream components of the process control system. However, in some examples, the filters become clogged or saturated with the dirt, oil and other debris. As the filter becomes congested with particulate, the flow of process fluid through the filter decreases and, thus, the regulator is not able to effectively regulate the pressure of the process fluid. Currently, process control system personnel (e.g., operators) change/replace the filters after a noticeable impact has occurred (e.g., a significant decrease in normal operating conditions).

SUMMARY

An example regulator includes a body having an inlet and an outlet and a flow control member interposed between the inlet and the outlet to regulate a fluid pressure at the outlet. The example regulator also includes a filter disposed between the inlet and the flow control member and a detector having a first measurement point upstream from the filter and a second measurement point downstream from the filter and upstream from the flow control member.

Another example regulator includes a first body portion having a fluid at a first pressure and a second body portion having a fluid at a second pressure lower than the first pressure. The first body portion and the second body portion are separated by a flow control member. The example regulator also includes a filter disposed in the first body portion and a detector having a first measurement point in the first body portion before the filter and a second measurement point after the filter and before the flow control member.

In yet another example, an apparatus includes a body having an inlet and an outlet defining a fluid flow passageway and a flow control member interposed between the inlet and the outlet to control a pressure of the fluid at the outlet. The example apparatus also includes a filter disposed between the inlet and the flow control member and means for measuring a parameter of the fluid across the filter.

DETAILED DESCRIPTION

Figure 1:
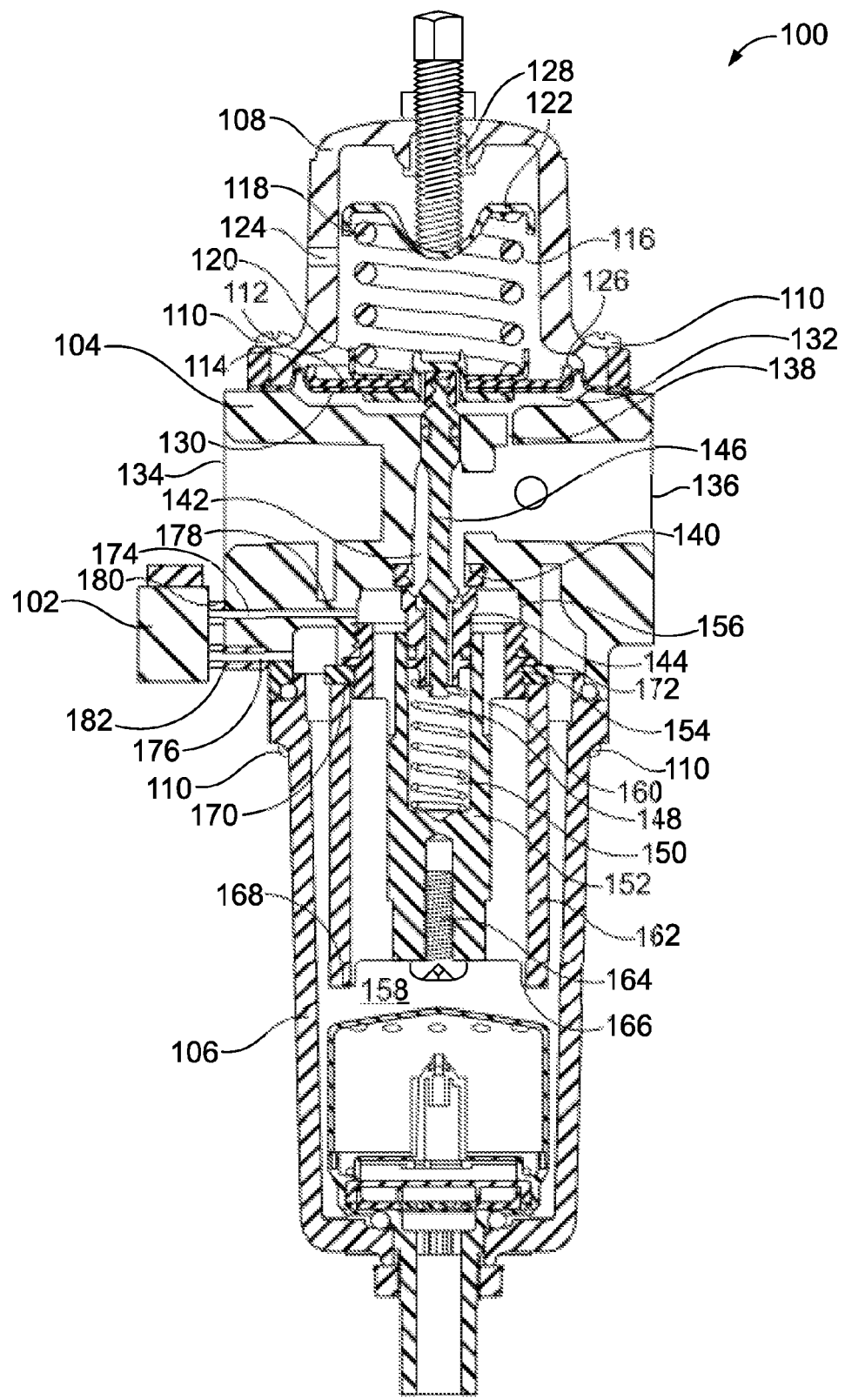
FIG. 1 illustrates a cross-sectional view of an example fluid regulator implemented with an example filter condition detector.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

In general, fluid regulators modulate the flow of fluid in accordance with a sensed downstream pressure to maintain process system pressures within acceptable and/or constant pressure limits. Fluid regulators typically regulate the flow and pressure of process fluid in response to a difference between an outlet fluid pressure (i.e., a force applied to one side of a diaphragm) and a pre-set control force (i.e., a force applied to another side of the diaphragm) to vary the flow of fluid through the regulator to achieve a substantially constant outlet pressure.

Fluid regulators typically include a diaphragm operatively coupled to a valve plug via a diaphragm plate and a valve stem. The diaphragm moves in a rectilinear path in response to a difference in force between a force exerted by the pressure of the fluid at the outlet and a pre-set force (e.g., set via a spring). Movement of the diaphragm causes the valve plug to move away from or toward a valve seat to allow or restrict the flow of fluid through an orifice and, thus, between the inlet and the outlet of the regulator.

Fluid regulators often employ a filter to capture (e.g., clean, sift, remove) particulate in an upstream chamber before the fluid flows through the orifice to a downstream chamber and the outlet. In some instances, the filter becomes clogged and adversely affects the flow and pressure of the fluid through the regulator. Once a filter becomes clogged, an operator must remove and change/clean the filter. However, by the time the filter becomes noticeably clogged, the regulator operations have already been negatively affected.

The example fluid regulators described herein advantageously utilize example detectors (e.g., a differential pressure gauge, a differential pressure transducer) to measure a parameter (e.g., a pressure difference across the filter) to indicate to what degree the filter has become clogged or restricted with particulate. In general, the example detectors measure the pressure of the process fluid at a first point upstream from the filter and a second point downstream from the filter to determine a difference in pressure across the filter. In some examples, the detector includes a visual indicator such as, for example, a color-coded gauge to display the pressure drop across the filter. As the pressure difference between the two points increases, the readout of the indicator increases and, thus, can alert operators to how dirty or clogged the filter has become. Such an indication may also enable operators to determine or estimate the amount of remaining useful life of the filter and/or when maintenance will be needed. In other examples, the detector includes a differential pressure transducer to convert the pressure difference into an electronic signal that may be sent, for example, to a control room for processing and readout. In such examples, an electronic output displays the pressure difference that will alert operators of how clogged or restrictive the filter has become.

FIG. 1 illustrates a cross-sectional view of an example fluid regulator 100 implemented with an example detector 102 described herein. In the example shown, the fluid regulator 100 includes a body 104, which includes a drip well 106 (e.g., a lower body) and a spring casing 108 (e.g., an upper body) that are coupled together via a plurality of fasteners 110. A diaphragm 112 is captured between the body 104 and the spring casing 108. The spring casing 108 and a first side 114 of the diaphragm 112 define a first chamber 116. A spring 118 is disposed within the spring casing 108 between a first spring seat 120 and an adjustable second spring seat 122. In this example, the first chamber 116 is fluidly coupled to, for example, the atmosphere, via an aperture 124.

The first spring seat 120 is coupled to a diaphragm plate 126 that supports the diaphragm 112. A spring adjuster 128 (e.g., a screw) engages the second spring seat 122 to enable adjustment of the length of the spring 118 (e.g., to compress or decompress the spring 118) and, thus, adjustment (e.g., to increase or decrease) of the amount of a pre-set force or load that the spring 118 exerts on the first side 114 of the diaphragm 112.

The body 104 and a second side 130 of the diaphragm 112 at least partially define a second chamber 132. The body also defines an inlet 134 and an outlet 136. The second chamber 132 is fluidly coupled to the outlet 136 via a channel 138. A valve seat 140 is disposed within the body 104 and defines an orifice 142 between the inlet 134 and the outlet 136. A valve plug 144 (e.g., a flow control member) is operatively coupled to the diaphragm 112 via a valve stem 146 and the diaphragm plate 126.

In the illustrated example, a second spring 148 is disposed within a cavity 150 of a spring retainer 152 to bias the valve plug 144 toward the valve seat 140. In the example shown, the spring retainer 152 has an outer flange portion 154 that couples (e.g., via threads) to a bore 156 formed in the body 104. When the spring retainer 152 is coupled to the body 104, the spring retainer 152 extends downward into a third chamber 158 defined by the body 104 and drip well 106. The spring retainer 152 also includes a plurality of channels 160 to create a flow path for process fluid to flow from the third chamber 158, through the channels 160 of the spring retainer 152, into the bore 156, and up through the orifice 142 when the valve plug 144 is not engaged with the valve seat 140. In the illustrated example, the valve plug 144 is engaged with the valve seat 140 to provide a tight seal to prevent fluid flow between the inlet 134 and the outlet 136. The spring rate of the second spring 148 is typically substantially smaller relative to the spring rate of the spring 118.

In the example shown, the fluid regulator 100 includes a filter 162 disposed within the third chamber 158. A filter retainer screw 164 is threadably coupled to the spring retainer 152 and holds a filter retainer 166 against a first end 168 (e.g., a bottom end) of the filter 162. A second end 170 (e.g., a top end) of the filter 162 is to engage the body 104 surrounding the bore 156. In the example shown, a gasket 172 is disposed between the second end 170 of the filter 162 and the body 104. In the example shown, the filter 162 has a circular cross-section. However, in other examples, the filter 162 may have other cross-sectional shapes such as, for example, a square, a rectangle, an oval or any other shape allowing the filter 162 to be disposed within the fluid regulator 100. In some examples, the filter is comprised of plastic, glass or stainless steel.

In operation, the inlet 134 is in fluid communication with, for example, an upstream fluid distribution source that provides fluid having a relatively high pressure. The outlet 136 is in fluid communication with a downstream demand source, pressure regulator, or any other custody point that demands process fluid at a desired (e.g., a lower) pressure.

The fluid regulator 100 typically regulates the upstream pressure of the fluid at the inlet 134 to provide or develop a desired pressure at the outlet 136. Thus, the fluid entering the inlet 134 and flowing through the third chamber 158 (e.g., a first body portion) is typically at a higher pressure than the fluid in the second chamber 132 (e.g., a second body portion) and exiting the outlet 136. To achieve a desired outlet pressure, the spring 118 exerts a force on the first side 114 of the diaphragm 112 which, in turn, positions the valve plug 144 relative to the valve seat 140 to restrict the flow of the process fluid between the inlet 134 and the outlet 136. Thus, the outlet or desired pressure is dependent upon the amount of pre-set force exerted by the spring 118 to position the diaphragm 112 and, thus, the valve plug 144 relative to the valve seat 140. The desired pressure set point may be configured by adjusting the force exerted by the spring 118 on the first side 114 of the diaphragm 112 via the spring adjuster 126.

In operation, high pressure fluid enters the regulator 100 at the inlet 134 and flows into the third chamber 158. The high pressure fluid flows through the filter 162 and into the bore 156 via the channels 160 in the spring retainer 152. When the downstream demand increases, the pressure of the fluid at the outlet 136 decreases and the second chamber 132 senses the decreasing pressure of the process fluid at the outlet 136 via the channel 138. When the force exerted on the second side 130 of the diaphragm 112 by the pressure of the fluid in the second chamber 132 decreases below the pre-set force exerted by the spring 118 on the first side 114 of the diaphragm 112, the spring 118 causes the diaphragm 112 to move toward the second chamber 132. When the diaphragm 112 moves toward the second chamber 132, the valve plug 144 moves away from the valve seat 140 (via the valve stem 146) to allow fluid to flow through the orifice 142 between the inlet 134 and the outlet 136 (e.g., an open position), thereby causing the pressure at the outlet 136 to increase.

Conversely, as the outlet 136 or downstream demand decreases or is shut-off, the pressure of the process fluid at the outlet 136 increases. As noted above, the increasing fluid pressure at the outlet 136 is registered in the second chamber 132 via the channel 138 and exerts a force on the second side 130 of the diaphragm 112. When the pressure of the fluid in the second chamber 132 exerts a force on the second side 130 of the diaphragm 112 that equals or exceeds the pre-set force exerted by the spring 118 on the first side 114 of the diaphragm 112, the diaphragm 112 moves toward the first chamber 116 (e.g., an upward direction against the force exerted by the spring 118 in the orientation of FIG. 1). When the diaphragm 112 moves toward the first chamber 116, the diaphragm 112 causes the valve plug 144 (e.g., via the stem 146) to move toward the valve seat 140 to restrict the flow of fluid through the orifice 142. The second spring 148 biases the valve plug 144 toward the valve seat 140 to sealingly engage the valve seat 140 (e.g., in a closed position) to substantially prevent fluid flow through the orifice 142 between the inlet 134 and the outlet 136 and, thus, reduce supply of the pressure to the downstream source (i.e., a lock-up condition). A lock-up condition of the fluid regulator 100 occurs when the valve plug 144 sealingly engages the valve seat 140 to provide a tight seal and prevent fluid flow between the inlet 134 and the outlet 136.

However, as described above, the filter 162 often becomes increasingly clogged as particulate (e.g., oil, dirt, debris) in the process fluid is caught in the filter 162. Eventually the filter 162 may become significantly clogged such that particulate caught in the filter 162 decreases the flow of fluid across the filter 162. In the example shown, the detector 102 is in communication with the process fluid in the regulator 100 via a first channel 174 and a second channel 176. The first channel 174 is an aperture formed in the body 104 that connects the bore 156 to the outside of the body 104. The process fluid in the bore 156 is downstream from the filter 162 and upstream from the orifice 142. In other words, the fluid inside the bore 156 is still high pressure fluid upstream from the valve plug 144 and valve seat 140. The channel 174 is fluidly isolated from the process fluid upstream from the filter 162 by a connector 178 (e.g., a tube, a sleeve, a channel, a pipe) that connects the outside of the body 104 and the bore 156.

The second channel 176 is an aperture formed in the body 104 that connects the outside of the body 104 with the fluid in the third chamber 158 upstream from the filter 162. In the example shown, the detector 102 is coupled to the first channel 174 and the second channel 176 via hoses or tubing 180, 182, respectively. In some examples, the hoses 180, 182 are connected to the outside of the body 104 and the detector 104 via fittings (e.g., threaded fittings). The detector 102 measures the pressure at a first point (e.g., the fluid in the bore 156 via the channel 174) downstream from the filter 162 and a second point (e.g., the fluid in the third chamber 158 outside of the filter 162) upstream from the filter 162. In some examples, with a clean filter, the pressure difference between the first point and the second point is minimal (e.g., substantially zero, negligible). However, as the filter 162 becomes clogged with particulate, the pressure differential across the filter 162 increases, such that the pressure at the first point (e.g., the fluid in the bore 156, the fluid in the channels 160, etc.) is lower than the pressure at the second point (e.g., the fluid in the chamber 158 upstream from the filter 162). In some examples, the detector 102 includes a visual gauge such as, for example, a color-coded gauge like that show in FIG. 4. In other examples, the detector 102 includes a transducer, which converts the pressure difference into an electrical signal and sends that signal to a control room for processing. In some examples, with a clean filter, there may be an existing or normal operating pressure drop across the filter 162. This existing pressure differential may depend on, for example, the type of filter, the type and size of the regulator, the flow rate of the process fluid and/or other variables affecting the flow of process fluid through the filter 162. In some examples, where a pressure differential already exists across the filter 162, the detector 102 may output only the difference between the increased pressure differential (e.g., from a clogged filter) and the existent pressure differential (e.g., the normal operating pressure differential). In other words, in some examples, the detector 102 produces an output (e.g., an electrical signal from a transducer) when the pressure differential exceeds a predetermined value or threshold pressure differential. In some such examples, the detector 102 may be set to indicate only this additional pressure differential exceeding the predetermined value.

In the example shown, the first channel 174 and the second channel 176 are aligned vertically on the same side of the fluid regulator 100. However, in other examples, such as those illustrated in FIGS. 2-4, the first and second channels 174, 176 are offset (i.e., not vertically aligned), so long as one channel connects to the process fluid downstream from the filter 162 and another channel connects to the process fluid upstream from the filter 162. In the example shown, the valve plug 144 (e.g., the flow control member) includes channels that fluidly connect the process fluid at the outlet 136 (e.g., the process fluid in the second chamber 132) and process fluid in the cavity 150 of the spring retainer 152. In some examples, this type of the valve plug configuration is considered balanced because the pressure of the process fluid at the outlet 136, which affects the pressure on the top of the valve plug 144 (e.g., the portion of the valve plug 144 that engages the valve seat 140), is substantially the same as the pressure in the cavity 150 of the spring retainer 152, which affects the pressure on the bottom of the valve plug 144. Therefore, in a balanced valve plug configuration, such as that shown in FIG. 1, the pressure of the process fluid at the inlet 134 (e.g., in the third chamber 158) has minimal effect on the valve plug 144 and, thus, the pressure of the process fluid at the outlet 136 is less affected by changes in pressure at the inlet 134. Although the detector 102 is shown and described in connection with a balanced type fluid regulator, the detector 102 may be similarly incorporated into an unbalanced type fluid regulator and/or any other type of fluid regulator having a filter. In an unbalanced fluid regulator, the pressure of the process fluid at the outlet is not substantially equalized with the pressure of the process fluid acting on the bottom or back end of the valve plug and, thus, changes in the pressure of the process fluid at the inlet exhibit greater changes to the pressure of the process fluid at the outlet.

Figure 2:
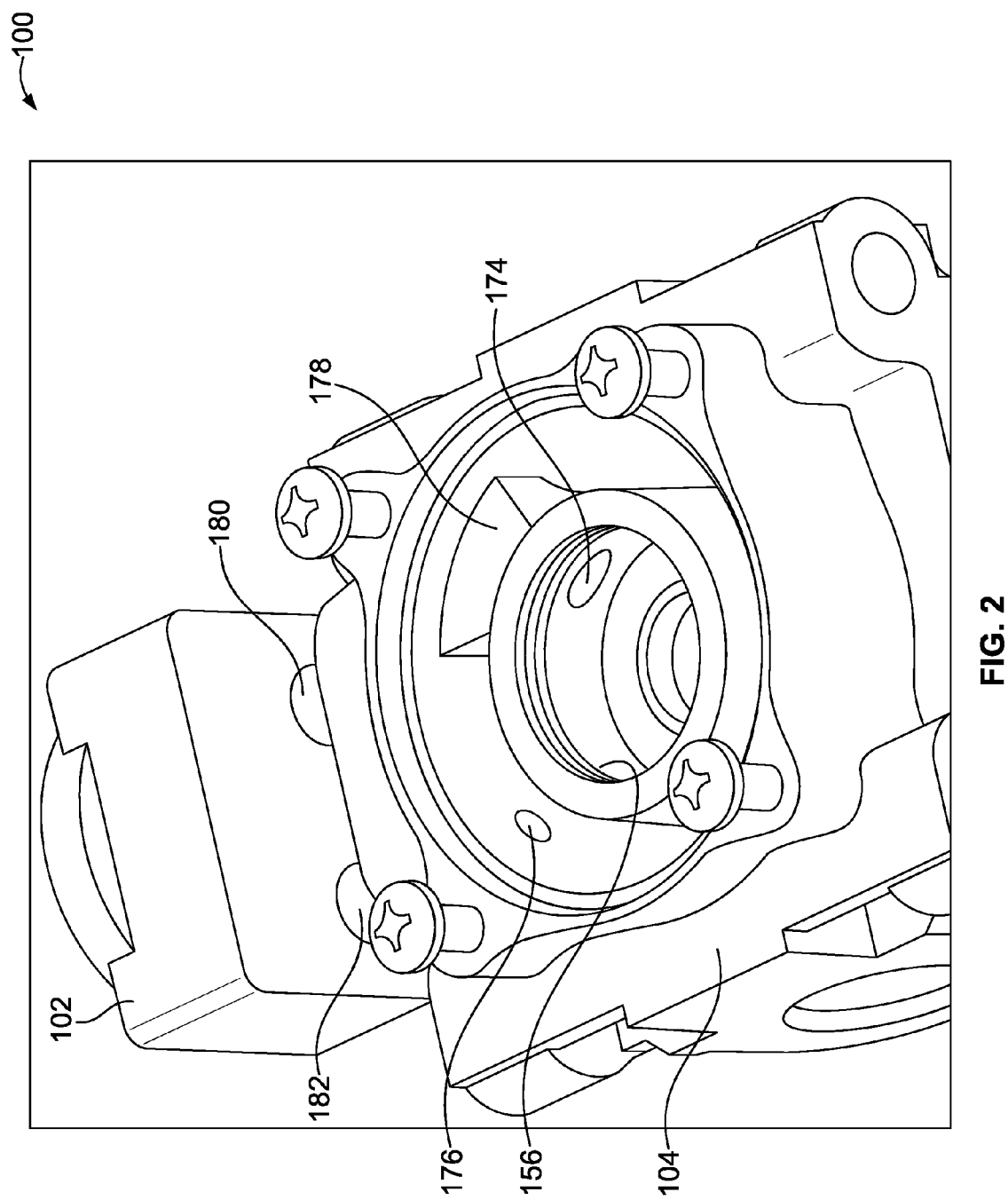
FIG. 2 illustrates a bottom view of the example fluid regulator of FIG. 1 in a partially assembled state.

FIG. 2 illustrates a bottom partially disassembled view of the body 104 of the example fluid regulator 100. The drip well 106, the filter 162 and the spring retainer 152, along with their respective components, have been removed for a more direct view. As shown, the detector 102 is coupled to an outside surface of the body 104. In some examples, the detector 102 is coupled to the outside of the body by mechanical fasteners (e.g., bolts, screws, etc). In other examples, the detector 102 is coupled to the outside of the body 104 only by the hoses 180, 182.

In the example shown, the first hose 180 and the second hose 182 operate to connect the detector 102 with the first channel 174 and the second channel 176. The first channel 174 passes through the connector 178, which fluidly isolates the first channel 174 from the process fluid in the third chamber 158 upstream from the filter 162 (shown in FIG. 1). The first channel 174 connects the detector 102 to the bore 156 to measure the pressure of the process fluid within the bore 156 (e.g., downstream from the filter 162 and upstream from the orifice 142, as shown in FIG. 1). The second channel 176 connects the detector 102 to the process fluid within the third chamber 158 (e.g., upstream from the filter 162 shown in FIG. 1). As shown in this example, the first channel 174 and the second channel 176 are offset from each other. As illustrated, the connector 178 has a quadrilateral cross-section. However, in other examples, the connector 178 may have any other shaped cross-section so long as the walls of the connector 178 fluidly isolate the first channel 174 from the high pressure fluid upstream from the filter 162. In some examples, the connector 178 is a solid unitary piece formed with the body 104. In other examples, the connector 178 is a separate component that is coupled to the inner walls of the body 104 in the area defined by the third chamber 158 (shown in FIG. 1).

Figure 3:
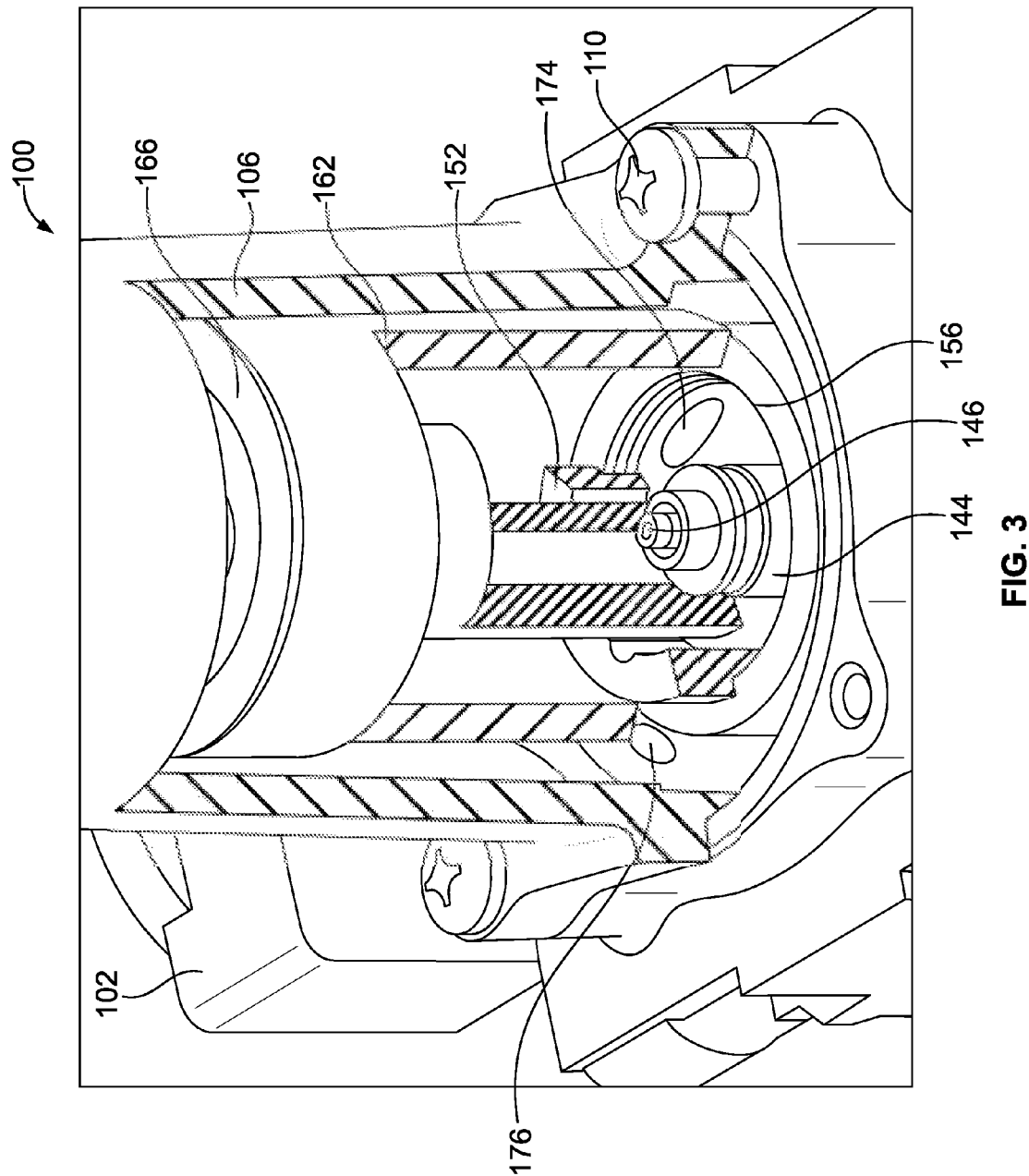
FIG. 3 a partially sectioned view of the example fluid regulator of FIG. 1.

FIG. 3 illustrates the bottom of the fluid regulator 100 with wall sections removed from the drip well 106, the filter 162 and the spring retainer 152 to expose the first channel 174 and the second channel 176. As shown, the filter retainer 166 holds the filter 162 against the body 104 around the bore 156. The spring retainer 152 is threadably coupled within the bore 156 and slidably receives the valve plug 144 via the valve stem 146. The first channel 174 forms a connection between the inside of the bore 156 and the outside of the body 104 where the detector 102 is to measure the pressure of the process fluid downstream from the filter 162 and upstream from the orifice 142 (shown in FIG. 1). The second channel 172 forms a connection between a portion of the third chamber 158 (e.g., upstream from the filter 158) and the outside of the body 104 where the detector is to measure the pressure of the process fluid upstream from the filter 162. In the example shown, fasteners 110 couple the drip well 106 to the body 104.

Figure 4:
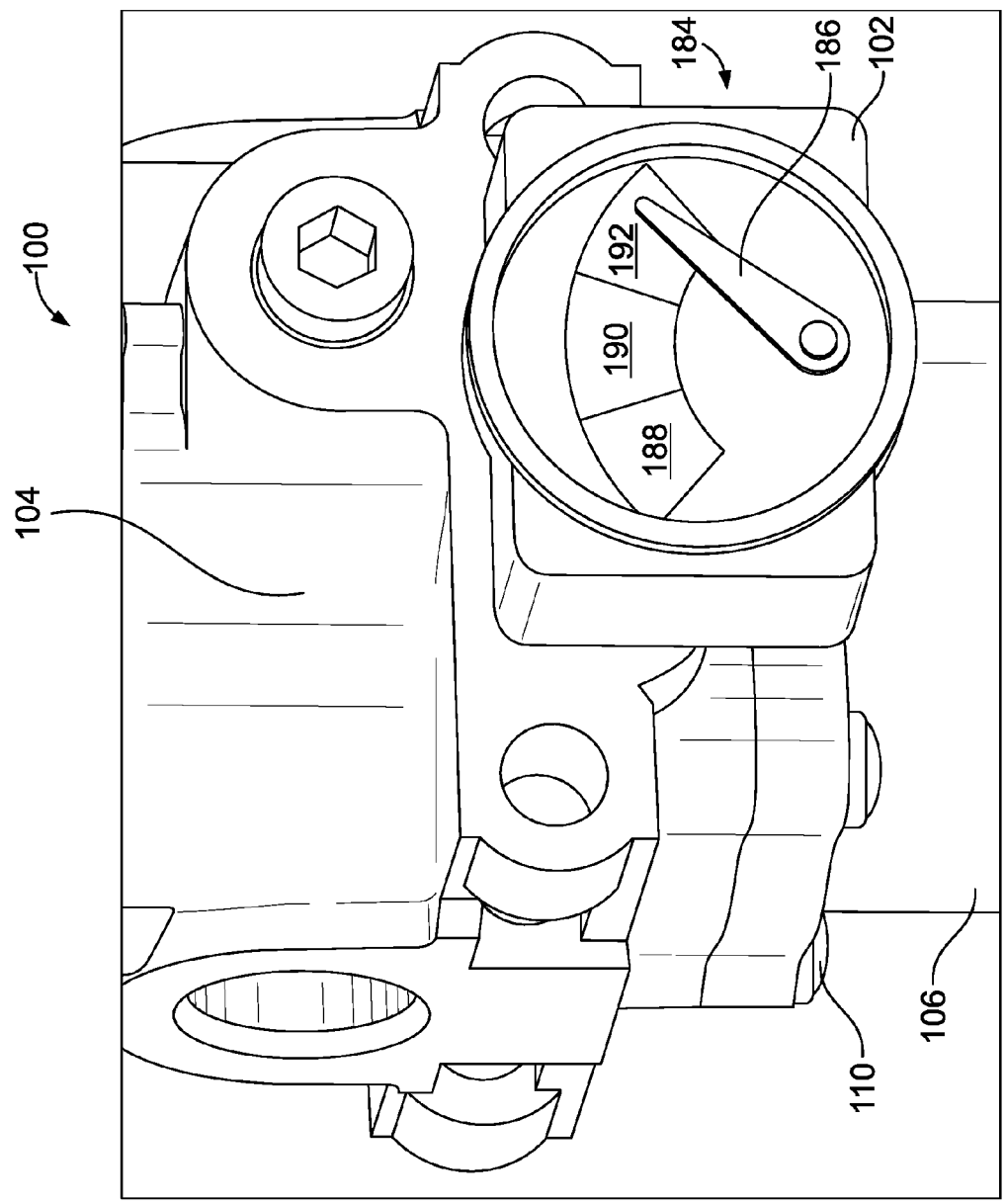
FIG. 4 illustrates a side view of the example fluid regulator of FIG. 1.

FIG. 4 illustrates a side view of the example fluid regualtor 100 with the example detector 102 coupled to the outside of the body 104. As shown in the example, the fasteners 110 couple the drip well 106 to the body 104. In the example shown, the detector 102 includes a visual indicator 184 having a needle 186 and three ranges, 188, 190, 192, which may be, for example, differently colored for clarity. In this example, the needle 186 rotates (e.g., clockwise) as the pressure difference between the process fluid upstream from the filter 162 (e.g., the process fluid in the third chamber 158 and at the inlet 134) and the downstream from the filter 162 (e.g., the process fluid in the bore 156) increases. In some examples, the ranges 188, 190, 192 include different colors to indicate the level of pressure differential (i.e., the amount the filter 162 is clogged with particulate). For example, one range 188 may be green to indicate the filter is unclogged (e.g., substantially unrestrictive), another range 190 may be yellow to indicate the filter is becoming clogged and the fluid regulator should be monitored (e.g., proceed with caution) and yet another range 192 may be red to indicate the filter is restricted (e.g., a dangerous condition, change as soon as possible). In other examples, other types of visual indicators or gauges may be used to indicate the difference in pressure between the first point and the second point.

The example fluid regulator 100 described herein utilizes a detector and a series of measurement points to measure the pressure differences across a filter in the fluid regulator 100. In some examples, the detector uses a visual indicator (e.g., a gauge) to alert operators of how clogged or restricted a filter has become. In other examples, the detector employs a pressure differential transducer to output an electrical signal that may be sent, for example, to a process control center for processing and monitoring. The use of the detector decreases the risk of a filter becoming overly clogged and negatively affecting the process control system.

Although certain example apparatus have been described herein, the scope of coverage of this patent is not limited thereto. On the contrary, this patent covers all methods, apparatus, and articles of manufacture fairly falling within the scope of the appended claims either literally or under the doctrine of equivalents.

What is claimed is:

1. A regulator comprising:
    a body having a fluid flow passageway forming a fluid flow path between an inlet and an outlet, the passageway defining an orifice;
    a flow control member interposed between the inlet and the outlet and movable within the passageway to prevent or allow fluid flow through the orifice to regulate a fluid pressure at the outlet;
    a filter disposed in the fluid flow path between the inlet and the orifice, a first portion of the fluid flow path being between the inlet and the filter, and a second portion of the fluid flow path between the filter and the orifice; and
    a detector having a first measurement point in the first portion of the fluid flow path and a second measurement point in the second portion of the fluid flow path, the detector in communication with the second measurement point via a channel extending through the first portion of the fluid flow path.

2. The regulator of claim 1, wherein the detector comprises a differential pressure gauge.

3. The regulator of claim 1, wherein the detector comprises a pressure transducer.

4. The regulator of claim 1, wherein the detector is coupled to an outside surface of the body.

5. The regulator of claim 1, wherein the detector is to measure a pressure difference between the first measurement point and the second measurement point.

6. The regulator of claim 5, wherein the detector comprises a visual indicator that is to display the measured pressure difference.

7. The regulator of claim 1, wherein the detector is in fluid communication with the first measurement point.

8. The regulator of claim 7, wherein the detector is in fluid communication with the second measurement point.

9. A regulator comprising:
    a first body portion to receive a fluid at a first pressure;
    a second body portion to deliver a fluid at a second pressure lower than the first pressure, the first and second body portions defining a fluid flow passageway therethrough, the first body portion and the second body portion separated by a flow control member movable within the passageway relative to an orifice to prevent or allow fluid flow from the first body portion to the second body portion;
    a filter disposed in the passageway and coupled to the first body portion, the filter surrounding the orifice, a first cavity defined in the first body portion between an inlet of the passageway and the filter, and a second cavity in the first body portion defined between the filter and the orifice; and
    a detector having a first measurement point in the first cavity and a second measurement in the second cavity.

10. The regulator of claim 9, wherein the first measurement point comprises an aperture in an outside wall of the first body portion.

11. The regulator of claim 9, wherein the second measurement point comprises a fluidly isolated channel through the first cavity into the second cavity.

12. The regulator of claim 9, wherein the detector is coupled to an outside surface of the first body portion or the second body portion.

13. The regulator of claim 9, wherein the detector is to measure a parameter of the fluid in the first body portion.

14. The regulator of claim 13, wherein the measured parameter comprises a pressure across the filter.

15. The regulator of claim 9, wherein the detector is to indicate a pressure difference between the first measurement point and the second measurement point.

16. The regulator of claim 15, wherein the detector comprises a color-coded display.

17. An apparatus comprising:
   a body having a fluid flow passageway between an inlet and an outlet, the passageway defining an orifice;
   a flow control member interposed between the inlet and the outlet and movable within the passageway to prevent or allow fluid flow through the orifice to control a pressure of the fluid at the outlet;
   a filter disposed between the inlet and the flow control member; and
   means for measuring a parameter of the fluid across the filter, the means for measuring including (1) a first measurement point in a first section of the passageway between the inlet and the filter and (2) a second measurement point in a second section of the passageway between the filter and the flow control member, the second measurement point formed by a channel fluidly isolated from and extending through the first section of the passageway to connect the means for measuring and the second section of the passageway.

18. The apparatus of claim 17, wherein the means for measuring the parameter comprises a detector to measure a pressure difference between the first measurement point and the second measurement point.

19. The apparatus of claim 18, wherein the detector comprises a gauge to indicate the measured pressure difference between the first measurement point and the second measurement point.

20. The apparatus of claim 19, wherein the gauge comprises a color-coded display.

\* \* \* \* \*